United States Patent
Yiu

(12)
(10) Patent No.: US 6,258,324 B1
(45) Date of Patent: Jul. 10, 2001

(54) PIPETTE DISPENSING BLOCK

(76) Inventor: Felix H. Yiu, 17234 Bullock St., Encino, CA (US) 91316

( * ) Notice: Subject to any disclaimer, the term of this patent is extended or adjusted under 35 U.S.C. 154(b) by 0 days.

(21) Appl. No.: 09/268,244

(22) Filed: Mar. 15, 1999

(51) Int. Cl.$^7$ ................................ B01L 3/02; B01L 3/00; B01L 9/00
(52) U.S. Cl. .................... 422/100; 422/102; 422/104; 73/863.32; 73/864.13; 73/864.16; 73/864.17; 73/864.18
(58) Field of Search ..................... 422/100, 102, 422/104; 73/863.31, 863.02, 864.11, 864.13, 864.16, 864.17, 864.18

(56) References Cited

U.S. PATENT DOCUMENTS

| | | | |
|---|---|---|---|
| 3,650,306 | 3/1972 | Lancaster | 141/238 |
| 4,087,248 | 5/1978 | Miles | 23/230 B |
| 4,106,911 | 8/1978 | Marcelli | 23/259 |
| 4,258,761 | 3/1981 | Bennett, Jr. | 141/242 |
| 4,459,864 | 7/1984 | Cirincione | 73/863.32 |
| 4,498,510 | 2/1985 | Minshew, Jr., et al. | 141/27 |
| 4,599,220 | 7/1986 | Yonkers et al. | 422/100 |
| 4,602,517 | 7/1986 | Schultz | 73/864.16 |
| 4,607,526 | 8/1986 | Bachenheimer et al. | 73/432 PS |
| 4,675,163 * | 6/1987 | Mybeck | 422/100 |
| 4,903,765 | 2/1990 | Zunkel | 166/162 |
| 4,957,706 | 9/1990 | Romette et al. | 422/100 |
| 5,021,217 * | 6/1991 | Oshikubo | 422/100 |
| 5,061,449 * | 10/1991 | Torti et al. | 422/100 |
| 5,181,427 | 1/1993 | Elias et al. | 73/863.12 |
| 5,403,554 | 4/1995 | Freeman | 422/100 |
| 5,497,670 | 3/1996 | Carl | 73/863.32 |
| 5,525,302 * | 6/1996 | Astle | 422/100 |
| 5,663,511 | 9/1997 | Geiller | 73/864.62 |
| 5,770,160 * | 6/1998 | Smith et al. | 422/100 |
| 5,958,343 * | 9/1999 | Astle | 422/100 |
| 6,143,252 * | 11/2000 | Haxo, Jr. et al. | 422/131 |

* cited by examiner

Primary Examiner—Jill Warden
Assistant Examiner—Brian R. Gordon
(74) Attorney, Agent, or Firm—Cislo & Thomas LLP

(57) ABSTRACT

A pipette dispensing block has an improved piston seal and lift plate engagement/disengagement means. In a pipette dispensing block where a piston is used to create a pressure differential to aspirate or extract and dispense or eject fluid material, the maintenance of a vacuum or increased pressure is enhanced by a pair of O-ring seals engaging the piston. A reservoir separates the O-rings and is filled with a low vapor pressure lubricant such as silicone oil or grease. The lubricant is maintained in the reservoir by the O-rings and serves to enhance the vacuum seal while maintaining the O-rings in a pliable and resilient manner. The heads of the pistons are engraved or grooved to leave a circular central pillar surrounded above and below by the piston head and a lower intermediate piston pillar section. The individual pistons are arranged in straight rows so that a slat may slip through opposite pairs of opposing piston pillars thereby entrapping the pistons and preventing them from sliding past the lift plate as the lift plate is lifted upwardly. Shoulders present on the pistons below the lift plate serve to allow the lift plate to push the pistons into the cylindrical chambers of the head block so that a pipette dispenser is provided. The lift plate or portions thereof are then trapped between the slats and the piston shoulders, coupling the pistons to the lift plate. Upward and downward control is thereby established and maintained by the lift plate on the pistons.

18 Claims, 2 Drawing Sheets

PIPETTE DISPENSING BLOCK

BACKGROUND OF THE INVENTION

1. Field of the Invention

This invention relates to laboratory equipment, and more particularly to a pipette dispensing block used in biologically-related laboratories that aspirates and dispenses fluid volumes in a precise and controlled manner.

2. Description of the Related Art

Recently, biology has increasingly incorporated elements of basic molecular and atomic chemistry, yielding the field of biotechnology. The secrets nature has hidden in mammalian and other biology are increasingly being unraveled and discovered. With greater knowledge of molecular biochemistry, genefic structure and effect, coupled with the ability to reproduce biologically active molecules quickly and easily, a corresponding increase in research has demanded tools and equipment that are able to promote the investigative activities related to present day biotechnology.

U.S. Pat. No. 5,525,302 issued Jun. 11, 1996 to Astle for a Method and Device for Simultaneously Transferring Plural Samples sets forth machinery by which standard samples in a standard sample container can be transferred, aspirated, and dispensed in a highly-controlled manner. The Astle '302 patent is incorporated herein by this reference hereto.

In the Astle '302 patent, a pipette system (particularly that one which is shown in FIGS. 1B and 5 of the Astle '302 patent) is disclosed relating to the construction and operation of a pipette system. As shown in FIG. 5, internal and external reservoirs may serve to control fluid flow through the hollow tube piston 50 when the clamp mechanism 140 is opened by separating the rod 146 from the anvil 142.

In the Astle '302 patent, the lift plate 52 controls the relative position of the hollow tube piston 50 in its travel inside the cylindrical channel 60. The elastomeric O-ring 62 seals the cylindrical channel 60 so that a vacuum may be pulled on the pipette tip 70, thereby allowing it to aspirate or, conversely, dispense fluid.

Note should be taken that if the elastomeric O-ring 62 breaks down through wear or otherwise does not seal the cylindrical channel 60, gases such as air can flow into the cylindrical channel 60 and thereby defeat the vacuum pulled on the cylindrical channel 60 by the motion of the lift plate 52 and the hollow tube piston 50. The same is similarly true when pressure is applied via the piston 50.

Consequently, it can be seen that the elastomeric O-ring 62 is a weak link in the Astle '302 patent system. This weak link is known in the art and is currently addressed by the application of grease, oil, or the like adjacent the elastomeric O-ring 62 as it suffers wear, tear, abrasion, and deterioration throughout the useful life of the elastomeric O-ring 62.

The opposite end of the cylindrical channel 60 is sealed by the pipette tip 70 and a second sealing O-ring 66 in conjunction with the hollow cylindrical pin extension 64. FIG. 5 of the Astle '302 patent shows all these features.

Additionally, FIG. 5 of the Astle '302 patent shows the use of retaining rings 54, 56 of the upper and lower portions of the top end of the hollow tube piston 50. As the hollow tube piston 50 forms one of ninety-six (96) such hollow tube pistons in an 8×12 array of such pistons, it becomes a daunting, time-consuming, and tedious task to replace one or several of the hollow tube pistons 50. Additionally, in order to remove one single piston such as a central one of the hollow tube pistons 50, the entire lift plate 52 may be required to be lifted up and away from the head block 40. This causes each and every one of the hollow tube pistons 50 to be disengaged from the head block 40, breaking the seal formed in conjunction with the elastomeric O-ring seal 62. The retaining rings 54, 56 consequently limit the utility of the Astle '302 patent device by making access to individual pistons more difficult.

Consequently, it can be seen that the use of retaining rings (such as those indicated by reference numbers 54 and 56, and the Astle '302 patent) creates some drawbacks with respect to the useful life and easy repair of pipette systems such as that shown in the Astle '302 patent.

Other developments in the pipette dispensing art are known and are indicated in summary fashion below.

U.S. Pat. No. 4,087,248 issued to Miles on May 2, 1978 for a Multiple Assay Machine and Method has a motor-driven housing and a syringe battery. An upper platform is mounted on threaded bolts so as to be capable of vertical movement with the turning of the bolts. A retaining syringe plunger plate is secured to an upper platform. The syringe battery has a rectangular housing with an upper guide plate mounted on a housing ceiling having a plurality of channels for guiding plungers. The syringe plunger plate has a hollow center for receiving the plunger heads and holding them in a fixed position. To perform an immunoassay, the syringe battery is introduced into the motor driven housing by sliding the syringe plunger plate between the L-shaped arms of the upper platform.

U.S. Pat. No. 4,106,911 issued to Marcelli on Aug. 15, 1978 for a Device for Examining a Plurality of Microdoses of Liquid is a dispenser of micro-doses of liquids having a base plate with a frame having a vertical arm. A motor is provided with a vertical screw arranged to position a slide block having an extension in the form of a horizontal plate with which the ends of plunger rods of syringes are made fast by means of clips. The bodies of the syringes are made fast with a support. When the motor is running, it moves a nut along a screw and varies the distance between a plate (indicated by reference number 11) and a support, thus enabling the plunger rods to move inside the bodies of all the syringes.

U.S. Pat. No. 4,602,517 issued to Schultz on Jul. 29, 1986 for a Fluid Sampling Method and Apparatus contains a multiple syringe dispenser having a central block assembly, an actuator assembly, and a syringe clamp assembly. Block members of the clamping assembly have protective frictional pads affixed to the V-shaped slots to delicately grip the handles of syringe tubes. The block and actuator assembly provides for the intermittent moving of a drive rod that raises a syringe plunger support assembly having lower and upper plates. Slots in the lower plate allow the insertion of a plunger member whereby the enlarged disk-like ends of the plungers are held by a cushioning pad extending the length of the upper and lower plates. Plungers fit into a cylinder of the syringe and the plungers can all be raised or lowered simultaneously by means of the actuator. A thermally-releasable sample collecting device has an absorber tube with its small diameter front end supported by a locating collar having two (2) O-ring seals. A rearward locating collar has O-ring seals for supporting the larger diameter rear end portion of the absorber tube.

U.S. Pat. No. 5,497,670 issued to Carl on Mar. 12, 1996 for a Liquid Dispensing Apparatus Including Means for Loading Pipette Tips onto Liquid Dispensing Cylinders and Maintaining the Loading Force During the Apparatus Operation Cycle is directed to an apparatus for dispensing controlled amounts of liquid into receptacles. The apparatus has a plurality of plate members either fixed or movable for supporting and dispensing liquids through disposable pipette tips. Fixed cylinders and a cylinder plate are attached to a cylinder mounting plate fixed to shafts. Pistons move in a vertical direction within the fixed cylinders. Each piston passes through a Teflon® seal. The pistons are connected to a piston plate using a ball and socket mechanism to provide accurate alignment. Each piston is allowed to swivel from the center point of the ball joint. The ball ends of the pistons are attached to a movable piston plate. The piston and cylinder assembly can be removed from the apparatus with the piston plate fixed to a larger plate that slides up and down along the shafts.

Despite the foregoing development and advances in the pipette dispensing art, it remains a problem in the art, solved by the present invention, to maintain a proper vacuum seal for sliding pipette pistons as well as providing convenient and well-engineered components by which a lifting plate for such pipette pistons can have such pistons easily mounted and dismounted (attached and detached) to it.

SUMMARY OF THE INVENTION

The present invention remedies shortcomings and drawbacks found in the prior art by better preserving the airtight nature of the cylindrical channels through which hollow tube or other pistons move in a pipette block assembly. As set forth above, the preservation of the airtight seal is important to preserve the vacuum and pressure differential by which liquids may be aspirated or dispensed. As the volumes of fluids are often extremely small, in the micro-liter amounts, the preservation of an airtight seal and the vacuum pressure differential is an important feature of pipette dispensing apparatus.

In order to achieve this better airtight seal, a pair of offset O-rings is used near the go top of the head block where the piston enters into it. Between the two sealing O-rings, a reservoir is created which is filled with oil, grease, or the like to both lubricate the piston as well as to enhance the seal. With the foregoing system, the abrasion experienced by the single sealing O-ring in the Astle '302 patent (deteriorating the O-ring and its ability to maintain an airtight seal) is overcome by lowering the abrasion experienced by the dual sealing O-ring and by better preserving the airtight nature of the contact between the head block and the piston.

Additionally, as the pistons may require maintenance or the like, and in order to control single rows (and perhaps single columns) of pistons, the piston heads are grooved to receive a sliding slat that interconnects the individual pistons and forces them to move with the lifting plate. In order to disengage the lifting plate from the piston heads, the slats are removed by sliding them laterally and the lifting plate is removed from the array of piston heads. The ends of the pistons, adjacent to the grooved piston heads, have an outwardly circumferential shoulder that engages the underside of one of the lifting plate portions. The individual pistons are then trapped by one or more of the lifting plate portions as a part of the lifting plate is trapped between the groove-engaging slat and the pistons' outward shoulders.

By engraving the piston heads so that they are grooved to engage the slats, and by providing the outward shoulders, convenient means (greatly exceeding that of single or dual retaining rings) are provided by which the lifting plate may be disengaged from the pistons and individual piston rows may be disabled or disengaged from the lifting plate.

OBJECTS OF THE INVENTION

It is an object of the present invention to provide a better seal for pipette pistons in a pipette dispensing block.

It is another object of the present invention to provide easily engagable and disengagable engaging means by which pipette piston heads may be associated and attached to a lifting plate.

It is another object of the present invention to provide a more resilient and longer lasting vacuum seal between a pipette piston and its head block.

These and other objects of and advantages of the present invention will be apparent from a review of the following specification and accompanying drawings.

DESCRIPTION OF THE PREFERRED EMBODIMENT(S)

The detailed description set forth below in connection with the appended drawings is intended as a description of presently preferred embodiments of the invention and is not intended to represent the only forms in which the present invention may be constructed, used, and/or utilized. The description herein sets forth the functions and the sequence of steps for constructing and operating the invention in connection with the illustrated embodiments. However, it is to be understood that the same or equivalent funtions and sequences may be accomplished by different embodiments that are also intended to be encompassed within the spirit and scope of the invention.

Figure 1:
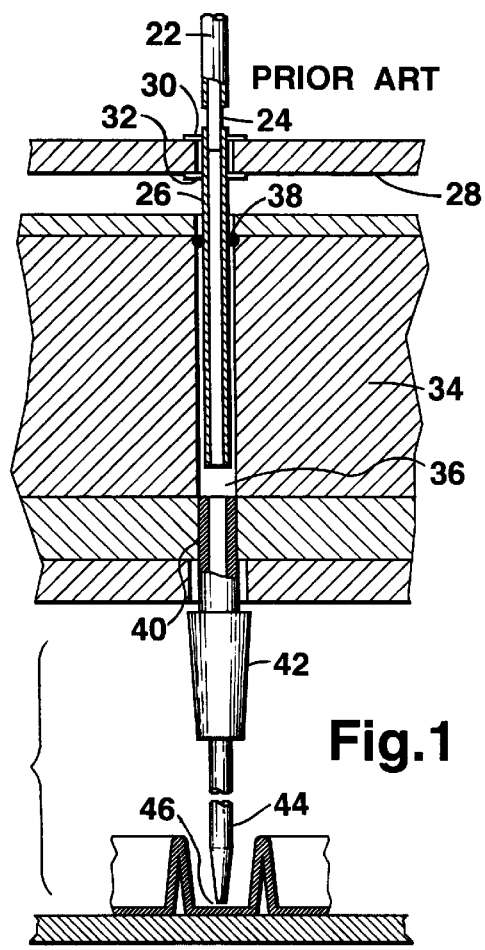
FIG. 1 is a side plan and partial cutaway view of a pipette piston dispensing arrangement corresponding closely to a significant portion of FIG. 5 in U.S. Pat. No. 5,525,302 issued to Astle on Jun. 11, 1996.
Figure 5:
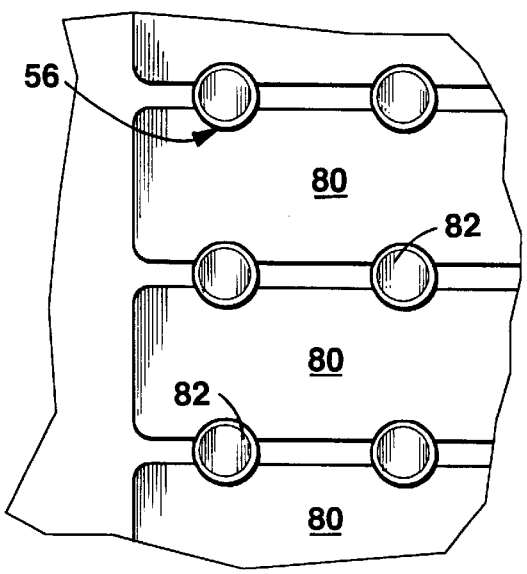
FIG. 5 is a partial and enlarged view of the piston head array with the groove-engaging slats intermediating individual piston heads corresponding to circle 5—5 of FIG. 4.

The shortcomings in the prior art are illustrated by FIG. 1 which corresponds in significant portion to FIG. 5 of the U.S. Pat. No. 5,525,302 issued to Astle on Jun. 11, 1996 (the "Astle '302 patent"). In FIG. 1, the Astle '302 patent pipette dispensing apparatus 20 is shown.

In FIG. 1, a flexible tube 22 leads into a hollow transition piece 24 which enters into the hollow tube piston 26. The hollow tube piston 26 is held in place by a lift plate 28 by upper and lower retaining rings 30, 32.

The hollow tube piston 26 moves into and out of the head block 34 at a cylindrical channel 36. A sealing O-ring 38 serves to seal the cylindrical channel 36 and its upper end To where the hollow tube piston 26 moves into and out of the head block 34.

A hollow cylindrical pin extension 40 engages a pipette tip 42 having an open end 46. The pipette tip 42 is often used in conjunction with a sample tray 44 in order to aspirate or dispense precise amounts of fluid.

As can be seen from FIG. 1, it is the open end 46 of the pipette tip 42 that allows for extraction or injection of fluid from the cylindrical channel 36 as controlled by the hollow cylinder piston 26. The hollow cylinder piston 26 may also be solid, however, in the Astle '302 patent, additional features were provided by such a hollow tube piston in conjunction with one or more reservoirs of fluid.

The ability to extract or aspirate fluid from the sample tray 44 is dependent upon the seal created by the sealing O-ring 38. As the piston 26 is withdrawn from the cylindrical channel 36, a pressure differential is created thereby forcing fluid from the sample tray 44 through the pipette tip 42 and ultimately into the cylindrical channel 36. If the seal provided by sealing O-ring 38 lacks integrity, leaks, or otherwise fails, the withdrawal of the piston 26 from the cylindrical channel 36 does not aspirate fluid from the sample tray 44. Instead, it pulls air into the cylindrical channel 36 past the sealing O-ring 38. Consequently, it is of great importance to make sure that the seal provided adjacent the top of the head block 34 with respect to the cylindrical channel 36 and in conjunction with the piston 26, maintains its integrity for the greatest amount of time in order to provide a longer useful life and better reliability for proper extraction and ejection of fluids.

Additionally, it can be seen that the upper and lower retaining rings 30, 32 provide difficult means by which the piston 26 is attached to the lift plate 28. While such retaining rings 30, 32 are convenient when used for an individual plunger 26, commonly, such plungers 26 are set forth in arrays of ninety-six (96) (8×12) which creates difficult spacing requirements in reaching the retaining rings, particularly for pistons 26 generally centrally located in the array. In fact, the other adjacent retaining rings 30, 32 and pistons 26 may need to be removed or moved in order to reach the particular piston of interest. It would be much better to provide a more convenient and simple means by which individual pistons can be disengaged from the lift plate 28 so that they may be adjusted, maintained, or fixed. Also such means could provide a better way to allow replacement or substitution of lift plates 28 or pistons 26.

Figure 2:
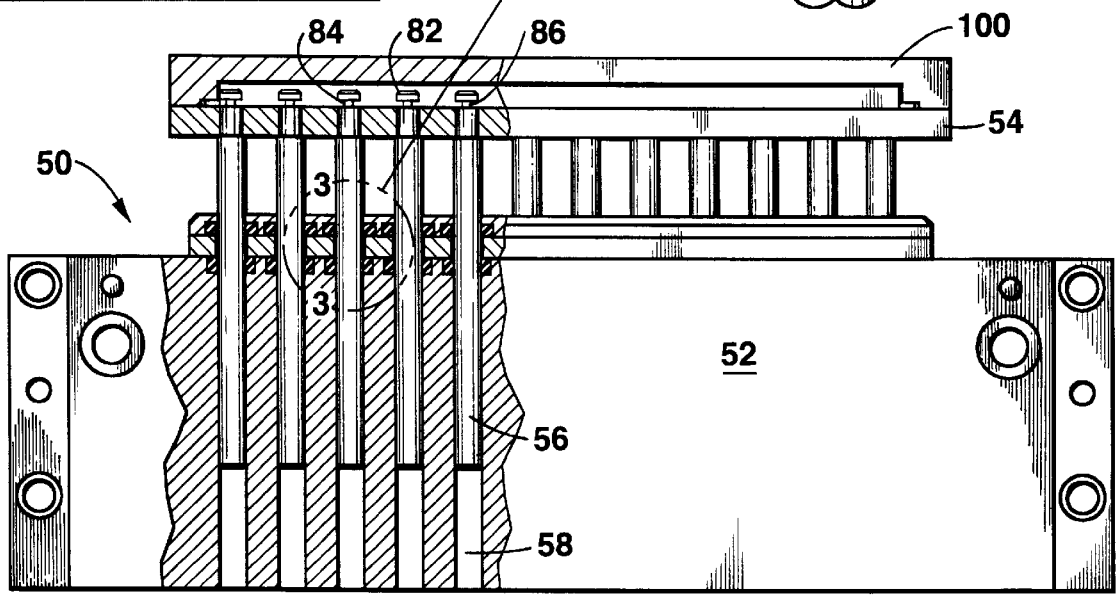
FIG. 2 is a side plan and partial cutaway view of the pipette dispensing block of the present invention showing the head block and individual pistons in their cylindrical channels.

The present invention is shown in partial view in FIG. 2. In FIG. 2, the pipette dispensing block of the present invention 50 has a head block 52 and a lift plate 54 as is common with such pipette dispensing apparatuses. A number of individual pistons 56 slidably travel through cylindrical channels 58 according to the relative positioning of the lift plate 54 with respect to the head block 52. Generally the head block 52 is maintained in a relatively stationary position and the lift plate 54 is moved vertically with respect to the head block 52 in order to control the disposition of the individual pistons 56 within the cylindrical channels 58. Assorted apertures for fixation or fastening of the head block 52 to framework or other supporting structures are shown at the lateral extremes of the head block 52 shown in FIG. 2.

Figure 3:
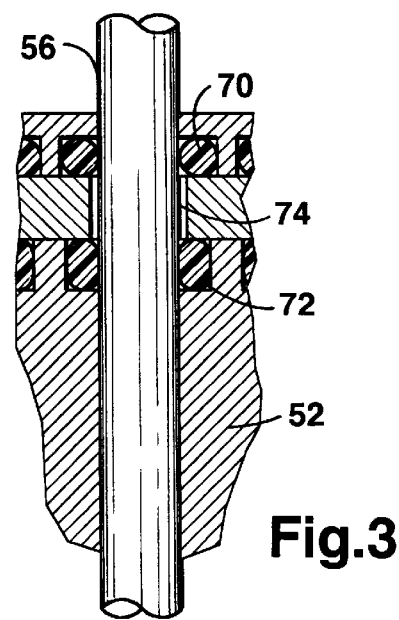
FIG. 3 is a partial cutaway and close-up view of the head block-piston interface corresponding to circle 3—3 in FIG. 2.

FIG. 3 shows an individual piston 56 at its juncture with the top of the head block 52. FIG. 3 corresponds to that portion of FIG. 2 indicated by circle 3—3.

As shown in FIG. 3, the piston 56 is circumscribed by a pair of O-rings: an upper O-ring 70 and a lower O-ring 72. Circumscribing the piston 56 between the upper and lower O-ring 70, 72 is a reservoir 74 defined by the interstitial space between the head of block 52 and the piston 56. This reservoir 74 may be filled with grease, oil, or the like, suitably manufactured to enhance preservation of the airtight vacuum seal created by the upper and lower sealing O-rings 70, 72. Low vapor pressure silicone grease or other low pressure greases and/or oils may be well suited to this purpose.

As the piston 56 slides upwardly or downwardly past the sealing O-rings 70, 72 and the low-vapor pressure lubricant-filled reservoir 74, the sides of the piston 56 are snugly engaged by the O-rings 70, 72. The grease or other lubricant is kept confined in the reservoir 74 by the O-rings 70, 72 as the piston 56 travels upwardly and downwardly past the reservoir 74.

When the piston 56 travels upwardly, any lubricant adhering to the side of the piston 56 is kept in the reservoir 74 by the upper O-ring 70. As the piston travels downwardly, the lower O-ring 72 prevents lubricant adhering to the exterior of the piston 56 from traveling past it, maintaining the lubricant in the reservoir 74. Some minor adherence of the grease to the exterior of the piston 56 may occur, taking some miniscule portion of the grease past the O-rings.

In this way, an airtight vacuum seal is provided about the sliding piston 56 by the upper O-ring 70, the low vapor pressure lubricant-filled reservoir 74 and the lower O-ring 72. The physical contact made between the sealing O-rings 70, 72 provides a vacuum seal which is enhanced by the low vapor pressure lubricant-filled reservoir 74. Beyond providing a viscous mechanical layer helping to preserve the seal, the low vapor pressure lubricant may also provide some additional resiliency and/or elasticity to the sealing O-ring 70, preventing them from cracking and wearing. The lubricant may also diminish the abrasion that may occur between the piston 56 and the O-rings 70, 72 as the piston 56 slides past the O-rings 70, 72.

As set forth in further detail below, the pistons 56 engage the lift plate 54 by means of slats 80. As shown in FIG. 2, the pistons 56 have piston heads 82. The piston heads 82 are separated from the other portions of the piston 56 by a piston head gap 84, there is being a small piston head pillar 86 attaching the piston head 82 to the remainder of the piston 56.

Figure 6:
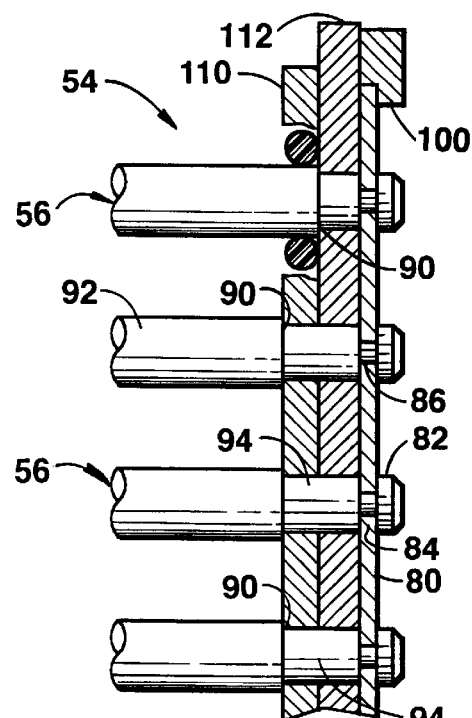
FIG. 6 is a side plan and partial cutaway view of the lifting plate shown in FIG. 4 taken along line 6—6.
Figure 4:
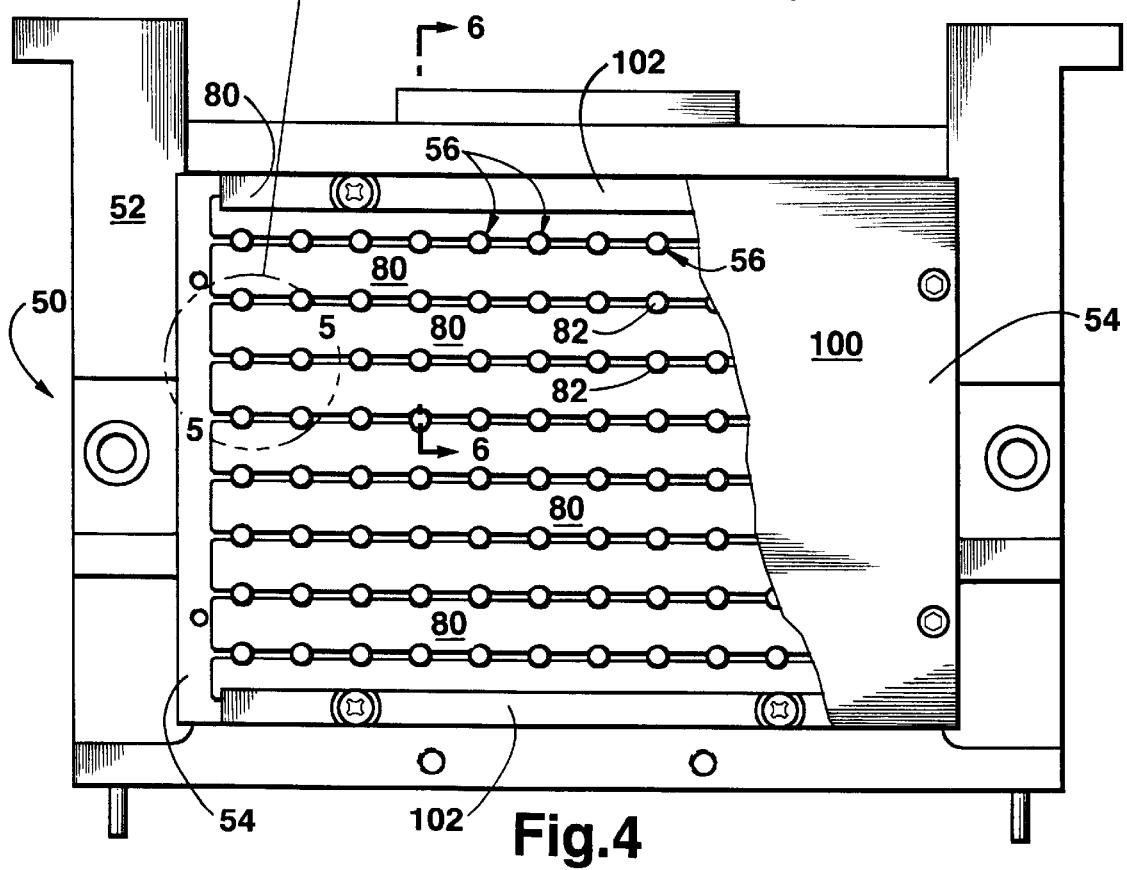
FIG. 4 is an overhead plan and partial cutaway view of the pipette dispenser of the present invention, the cutaway view showing the lift plate, the slats, and individual piston heads held thereby.

FIGS. 4–6 show the piston heads 82, the slats 80, and the engagement of the pistons 56 with the lift plate 54. Further, FIG. 6 shows the piston shoulders 90 as they rest against the underside of the lift plate 54. Intermediating the distance through which the piston 56 travels through the lift plate 54, between the piston head pillar 86 and the main body portion 92 of the piston 56, is an intermediate pillar section 94.

As shown in FIG. 4, the pistons 56 may be arranged in a standard 8×12 array so that eight dozen samples may be pipetted simultaneously. A top and restraining cover 100 of the lift plate 54 is shown in partial cutaway view revealing the underlying pistons 56 and the exposed piston heads 82 along with the intermediating sliding slats 80.

The slats 80 engage the pillar grooves or gaps 84 in a close manner. When the lift plate cover 100 is removed, the slats 80 may be removed from between the piston heads 82 by sliding them laterally. Generally, the slats 80 are trapped between two (2) adjacent rows of pistons 56. However, at the upper and lower ends (relative to FIG. 4), the first and last rows of pistons 56 do not have other adjacent piston rows.

Consequently, slat holders 102 are used that conform continuously to the grooves presented by the piston heads 82. Consequently, the pistons 56 on the first and last rows are also held in place on either side by slats 80 as the terminal slats are also held in place on both sides (on one side by a row of piston heads 82 and on the other side by the slat holders 102).

Due to the accuracy required in pipetting samples with pipette dispensers, the materials used in the present invention are generally materials easily sterilizable and chemically inert. Machined-aluminum, steel, and the like that are manufactured to close tolerances provide adequate materials and structures by which the stresses and forces arising from the use of the pipette dispensing block of the present invention may be accommodated and endured without breakage, damage, or extraordinary wear and tear. This is particularly true for the piston heads 82 where the piston head gap 84 about the piston head pillar 86 may be a point of weakness due to the thin nature of the piston head pillar 86. However, the materials currently used in the art appear to provide adequate support and structural integrity for use in the present invention.

As shown in FIG. 5, the slats 80 are held in place on either side by the piston heads 82. The slats 80 slide between the pistons 56 and are held in place by opposing pairs of piston head pillars 86 (not shown in FIG. 5, see FIGS. 2, 6). The piston head gaps 84 are generally the same height as the slats 80, or in close tolerance, only slightly exceeding such height.

The slats 80 hold the pistons 56 in place as the lift plate 54 lifts up and away from the head block 52. When the lift plate 54 descends, in order to eject or dispense fluid held in the cylindrical channels 58, the lift plate 54 presses down against the piston shoulders 90 in order to drive the piston forward and into the cylindrical channel 58. Consequently, the intermediate piston section 94 of the piston 56 is trapped inside the lift plate 54.

As shown relative to FIG. 6, the piston 56 cannot move to the right past the lift plate 54 as the shoulder 90 prevents passage of the piston through the lift plate 54. The piston 56 cannot move leftwardly relative to FIG. 6 through the lift plate 54 and the aperture there accommodating the intermediate pillar section 94 as the slat 80 prevents the piston head 82 from traveling to the left. However, once the slats 80 on both sides of the piston head 82 are removed, the piston head 82 may then travel through the piston aperture 104 present for each and every piston 56 in the array. The lift plate piston aperture 104 is of a diameter generally sufficient to accommodate the intermediate piston pillar section 94.

As shown in FIG. 6, the lift plate 54 may have two (2) apertured plates beyond the generally solid lift plate cover 100. The bottom lift plate 110 may generally engage the top portion of the main piston portion 92 at the shoulder 90.

The plates 112 and 110 may be integral as shown in FIG. 2 as opposed to separate as shown in FIG. 6. In the top piston, an O-ring is set into the bottom portion of lower plate 110 for each of the pistons 56 in order to seat each of the pistons 56 in a resilient manner with respect to the lift plate 54. The shoulder 90 may then engage a more interior abutment present in the lower plate 110. The upper plate 112 is adjacent and above the lower plate 110 and serves to provide a foundation upon which the slats 80 may rest as they engage the piston heads 82. In the alternative embodiment, the piston shoulders 90 may engage the underside of the upper plate 112 with the lower plate 110 providing room for an O-ring gasket or the like to resiliently hold in place the individual pistons 56.

By using the grooved piston head 82 and slat 80 arrangements set forth above, it becomes a much simpler task to engage or remove an individual piston 56, particularly pistons that are central to an 8×12, 16×24 or other array. The lift plate cover 100 is removed and thereby exposing the piston heads 82 and the slats 80. The slats 80 then slide laterally to disengage the individual piston heads 82, the slats 80 sliding through the grooves and generally out and away from the lift plate 54. The upper plate 112 (FIG. 6) may then be removed from the lower plate 110 once all of the slats 80 have been removed.

As seen in FIG. 6, upon removing the upper plate 112, the lower plate 110 is then exposed and may also be removed from the top of the pistons 56 and their array. Individual ones of the pistons 56 may then be withdrawn from the head block 52 in order to be replaced or repaired. The lower plate 110 may then be replaced upon the piston heads 82, with the optional gasket O-rings seating themselves in the bottom of the lower plate 110. The upper plate 112 may then be replaced upon the top of the piston array. The pistons 56 may then be arranged so that the piston heads 82 protrude up and away from the upper plate 112. The slats 80 may then be slid back into their position between the rows of piston heads 82, the slats 80 sliding through the close-tolerance gap defined between opposite pairs of piston head pillars 86.

While the present invention has been described with regards to particular embodiments, it is recognized that additional variations of the present invention may be devised without departing from the inventive concept.

What is claimed is:

1. A pipette dispensing block, comprising:
   a head block, said head block defining a channel, said channel having an upper end, said head block defining a reservoir adjacent said upper channel end;
   a piston, said piston slidably travelling through said channel;
   a first seal, said first seal adjacent said reservoir and providing a seal between said head block and said piston; and
   lubricant, said lubricant held in said reservoir; whereby said first seal provides an airtight vacuum seal about said piston adjacent said upper channel end.

2. The pipette dispensing block of claim 1, further comprising:
   a second seal, said second seal adjacent said reservoir on a side opposite to that of said first seal such that the reservoir is between said first and second seals.

3. The pipette dispensing block of claim 2, wherein said first and second seals further comprise O-rings.

4. The pipette dispensing block of claim 3, wherein said first and second seals suffer less where and tear from said sliding piston as contact between said first and second seals is lubricated by said lubricant, whereby said vacuum seal is maintained in a better and more enduring manner.

5. The pipette dispensing block of claim 4, wherein said lubricant is a low vapor pressure lubricant, whereby said lubricant does not tend to evaporate into said channel.

6. A pipette dispensing block, comprising:
   a head block, said head block defining a channel, said channel having an upper end;
   a piston, said piston slidably traveling through said channel;
   a first seal, said first seal adjacent said upper channel end and providing a seal between said head block and said piston; and
   a second seal, said second seal adjacent said first seal and providing a seal between said head block and said piston; whereby
   said first and second seals provide an airtight vacuum seal about said piston adjacent said upper channel end;
   said head block defining a reservoir adjacent said upper channel end, said reservoir between said first and second seals; and
   lubricant, said lubricant held in said reservoir; whereby said first and second seals contain said lubricant in said reservoir.

7. The pipette dispensing block of claim 6, wherein said first and second seals further comprise O-rings.

8. The pipette dispensing block of claim 7, wherein said first and second seals suffer less where and tear from abrasion from said sliding piston as contact between said first and second seals is lubricated by said lubricant, said vacuum seal is maintained in a better and more enduring manner, and said lubricant serves to maintain said first and second seals in a more resilient condition.

9. The pipette dispensing block of claim 8, wherein said lubricant is a low vapor pressure lubricant, whereby said lubricant does not tend to evaporate into said channel.

10. A pipette dispensing block having a lift plate, comprising:
    a piston, said piston having a head and defining a head groove adjacent to said head;
    a slat, said slat dimensioned in height to engage said piston head by passing through said piston groove; whereby
    said piston is held in place by said piston with respect to the lift plate.

11. The pipette dispensing block having a lift plate of claim 10, wherein said piston further comprises:
    a shoulder, said shoulder abutting an underside of the lift plate; whereby
    a lift plate portion is trapped between said slat and said shoulder, locking said piston to the lift plate.

12. The pipette dispensing block having a lift plate of claim 11, further comprising:
    said piston being one of several pistons in a first straight row; and
    said slat slidably trapped between said first straight row and a second straight row of pistons; whereby
    said pistons of said first and second straight rows are locked to the lift plate by said slat.

13. The pipette dispensing block having a lift plate of claim 12, wherein the lift plate further comprises:
    an upper plate, said upper plate defining an upper piston aperture through which said piston passes; and
    a lower plate, said lower plate adjacent and below said upper plate, said lower plate defining a lower piston aperture through which said piston passes; whereby
    said piston may be disposed by the lift plate by said upper and lower plates.

14. The pipette dispensing block having a lift plate of claim 13, further comprising:
    said lower plate defining a set-in or offset surrounding said piston; and
    an O-ring, said O-ring sitting in said offset and engaging said piston; whereby
    said piston is resiliently positioned by said O-ring in alignment with said upper and lower piston apertures.

15. The pipette dispensing block having a lift plate of claim 14, further comprising:
    said piston shoulder abutting said upper plate; whereby
    said piston is locked to said upper plate and the lift plate by trapping the upper plate between said piston shoulder and said slat.

16. A pipette dispensing block, comprising:
    a head block, said head block defining a channel, said channel having an upper end, said head block defining a reservoir adjacent said upper channel end;
    a piston, said piston slidably travelling through said channel, said piston having a head and defining a head groove adjacent to said head, said piston having a shoulder, said shoulder spaced away from said piston head;
    a lift plate, said lift plate having an upper plate and a lower plate, said lower plate adjacent and below said upper plate, said upper plate defining an upper piston aperture through which a first portion of said piston passes, said lower plate defining a lower piston aperture through which a second portion of said piston passes, said piston disposed by said lift plate by said upper and lower plates thereof;
    a first O-ring seal, said first seal adjacent said channel reservoir and providing a seal between said head block and said piston;
    a second O-ring seal, said second seal adjacent said channel reservoir on a side opposite to that of said first seal such that said channel reservoir is between said first and second seals;
    a low vapor pressure lubricant, said lubricant tending not to evaporate into said channel, said lubricant held in said reservoir
    a slat, said slat dimensioned in height to engage said piston head by passing through said piston groove to hold said piston in place with respect to the lift plate;
    said piston shoulder abutting an underside of said lift plate to trap a portion of said lift plate between said piston shoulder and said slat, locking said piston to the lift plate;
    said piston being one of several pistons in a straight row, said slat slidably trapped by said straight row so that said pistons of said straight row are releasably locked to said lift plate by said slat; whereby
    said first and second seals provide an airtight vacuum seal about said piston adjacent said upper channel end and said first and second seals suffer less wear and tear from said sliding piston as contact between said first and second seals is lubricated by said lubricant, said lubricant maintaining said vacuum seal in a better and more enduring manner by providing a greater mechanical barrier preserving said airtight vacuum seal, said lubricant lubricating and reducing abrasion between said sliding piston and said first and second seals; and whereby
    said slat provides convenient and easy engagement and disengagement of said piston by said lift plate.

17. The pipette dispensing block of claim 16, further comprising:
    said lower plate defining a set-in or offset surrounding said piston; and
    an O-ring, said O-ring sitting in said offset and engaging said piston; whereby
    said piston is resiliently positioned by said O-ring in alignment with said upper and lower piston apertures.

18. The pipette dispensing block of claim 17, further comprising:
    said piston shoulder abutting said upper plate at a bottom or lower portion thereof; whereby
    said piston is locked to said upper plate and said lift plate by trapping said upper plate between said piston shoulder and said slat.

* * * * *